US006627770B1

(12) United States Patent
Cheung et al.

(10) Patent No.: US 6,627,770 B1
(45) Date of Patent: Sep. 30, 2003

(54) METHOD AND APPARATUS FOR SEQUESTING ENTRAINED AND VOLATILE CATALYST SPECIES IN A CARBONYLATION PROCESS

(75) Inventors: Hung-Cheun Cheung, Corpus Christi, TX (US); Valerie Santillan, Friendswood, TX (US); Mark O. Scates, Friendswood, TX (US); Elaine C. Sibrel, Corpus Christi, TX (US); G. Paull Torrence, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 456 days.

(21) Appl. No.: 09/645,642

(22) Filed: Aug. 24, 2000

(51) Int. Cl.$^7$ ............................................... C07C 51/12
(52) U.S. Cl. ....................................................... 562/519
(58) Field of Search ......................................... 562/519

(56) References Cited

U.S. PATENT DOCUMENTS

| 4,127,506 A | | 11/1978 | Gray et al. ................. 252/431 |
| 4,139,688 A | | 2/1979 | Dixon ......................... 526/41 |
| 4,328,125 A | * | 5/1982 | Drago et al. |
| 4,615,806 A | | 10/1986 | Hilton ........................ 210/690 |
| 4,786,699 A | | 11/1988 | Nuber et al. ................. 526/229 |
| 5,131,943 A | * | 7/1992 | Allison et al. |
| 5,144,068 A | | 9/1992 | Smith et al. ................. 562/519 |
| 5,155,261 A | | 10/1992 | Marston et al. ............. 562/519 |
| 5,281,359 A | | 1/1994 | Scates et al. ................ 252/182 |
| 5,286,826 A | | 2/1994 | Shih et al. ................... 526/264 |
| 5,334,755 A | | 8/1994 | Yoneda et al. ............... 562/519 |
| 5,364,963 A | | 11/1994 | Minami et al. .............. 562/519 |
| 5,417,942 A | * | 5/1995 | Foos et al. |
| 5,466,874 A | | 11/1995 | Scates et al. ................ 562/519 |
| 5,625,095 A | * | 4/1997 | Miura et al. |
| 5,723,680 A | * | 3/1998 | Kormann et al. |
| 5,877,347 A | | 3/1999 | Ditzel et al. ................. 562/519 |
| 5,877,348 A | | 3/1999 | Ditzel et al. ................. 562/519 |
| 5,883,295 A | | 3/1999 | Sunley et al. ............... 562/519 |
| 5,892,110 A | | 4/1999 | Ramprasad et al. ........ 562/891 |
| 5,932,764 A | | 8/1999 | Morris et al. ................ 562/519 |
| 5,942,460 A | | 8/1999 | Garland et al. ............. 502/150 |

FOREIGN PATENT DOCUMENTS

| EP | 0 685 445 B1 | 5/1995 | ............ C07C/53/08 |
| EP | 0 728 729 B1 | 7/1995 | ............ C07C/53/08 |
| WO | 98/33590 | 8/1998 | ............ B01J/23/46 |
| WO | 98/57918 | 12/1998 | ............ C07C/51/12 |

OTHER PUBLICATIONS

Applied Homogeneous Catalyst With Organometallic Compounds, Cornils et al., Ed. (Bench Edition)(Wylie, Weinheim Federal Republic of Germany 2000), Chapter 2, Parts 2.1.2. and following, pp. 104–137.

* cited by examiner

*Primary Examiner*—Shailendra Kumar
*Assistant Examiner*—Paul A. Zucker
(74) *Attorney, Agent, or Firm*—M. Susan Spiering

(57) ABSTRACT

A method and apparatus for sequestering entrained or volatile catalyst species in a carbonylation process includes contacting the product stream with a vinyl pyridine or a vinyl pyrrolidone resin bed which is operative to sequester entrained or volatile catalytic species. The invention is particularly useful in connection with the iridium catalyzed carbonylation of methanol wherein the loss of entrained or volatile catalyst species depletes the catalytic content of the reactor. The resin may be digested in order to recover the catalytic metals.

15 Claims, 1 Drawing Sheet

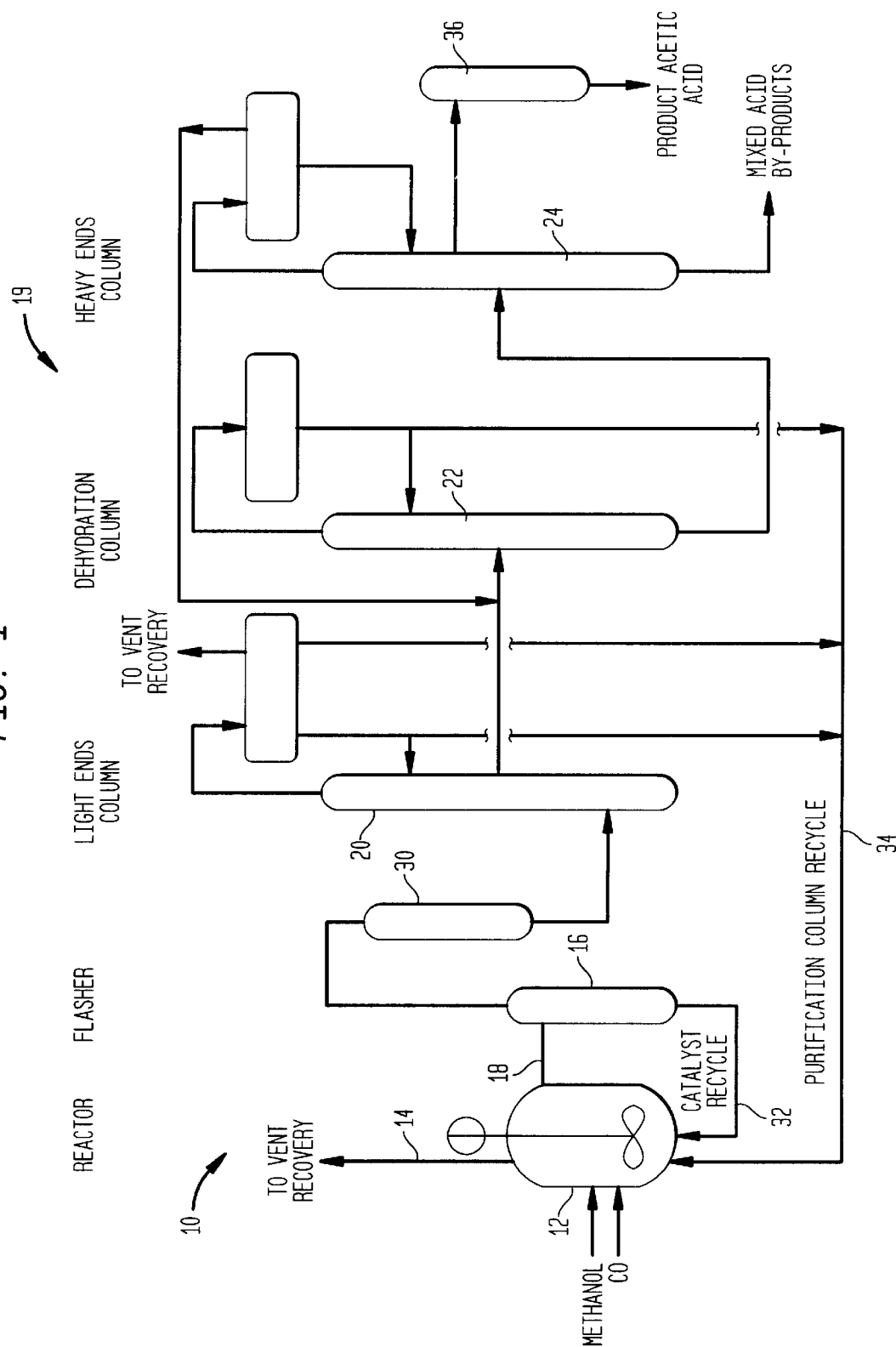

METHOD AND APPARATUS FOR SEQUESTING ENTRAINED AND VOLATILE CATALYST SPECIES IN A CARBONYLATION PROCESS

TECHNICAL FIELD

The present invention relates generally to carbonylation processes and specifically to a method of sequestering entrained or volatile group VIII metal catalysts in a carbonylation apparatus.

BACKGROUND ART

Carbonylation processes are well known in the art. Of particular commercial significance are processes for the carbonylation of methanol to make acetic acid and processes for the carbonylation of methyl acetate to make acetic anhydride. See Applied Homogeneous Catalyst With Organometallic Compounds, Cornils et al., Ed. (Bench Edition) (Wylie, Weinheim, Federal Republic of Germany 2000), Chapter 2, Parts 2.1.2 and following, pp. 104–137.

To make acetic acid, one method of choice involves carbonylating methanol in a homogeneous reaction medium wherein rhodium is utilized as a catalyst. This method is generally referred to in the art as the Monsanto process and was developed in the 1970's. A particularly preferred method is taught in U.S. Pat. No. 5,144,068 to Smith et al. In this so called "low water" process an alcohol such as methanol is reacted with carbon monoxide in a liquid reaction medium containing a rhodium catalyst stabilized with an iodide salt, especially lithium iodide along with alkyl iodide such as methyl iodide and alkyl acetate such as methyl acetate in specified proportions. With a finite concentration of water in the reaction medium, the product is the carboxylic acid instead of, for example, the anhydride. The reaction system of the '068 patent not only provides an acid product of unusually low water content at unexpectedly favorable rates, but also exhibits unexpectedly high catalyst stability. That is, the catalyst is resistant to catalyst precipitation out of the reaction medium.

Another method of choice for carbonylating methanol involves utilizing a homogeneous iridium catalyst in the reactor. There is disclosed, for example, in U.S. Pat. No. 5,883,295, to Sunley et al. a process for the production of acetic acid comprising carbonylating with carbon monoxide methanol and/or a reactive derivative thereof, in the substantial absence of a metal promoter and/or ionic iodide co-promoter in a carbonylation reactor containing a liquid reaction composition comprising an iridium carbonylation catalyst, methyl iodide co-catalyst, water, acetic acid, and methyl acetate wherein there is maintained in the liquid reaction composition: (a) water at a concentration of less than 5% by weight; (b) methyl iodide in a concentration of greater than 12% by weight and (c) in the carbonylation reactor a total pressure of less than 50 bar. See also U.S. Pat. No. 5,877,348 to Ditzel et al. and U.S. Pat. No. 5,877,347 also to Ditzel et al.

One drawback of the iridium catalyzed homogeneous system in particular is the tendency of the catalyst to form volatile species which leads to catalyst loss. See for example U.S. Pat. No. 5,942,460 to Garland et al. at Col. 4, lines 3 and following as well as U.S. Pat. No. 5,932,764 to Morris et al. at Col. 3, line 1 and following wherein it is stated:

. . . Preferably to prevent a significant increase in the volatility of the iridium catalyst and/or optional promoter the amount of carbon monoxide in the second liquid composition withdrawn from the second reaction zone should not be reduced too low, typically to maintain at least 20% by volume of the dissolved and/or entrained gases therein . . . .

As will be appreciated by one of skill in the art, there is always incentive for improvement to existing processes, for example the precipitation in the homogeneous rhodium system is constantly subject to improvement, whereas the volatility problem in the iridium system is constantly addressed. One method proposed and worked on extensively was to introduce a supported catalyst into carbonylation systems to avoid stability/volatility/and precipitation problems. For example, there is disclosed in U.S. Pat. No. 5,466,874 to Scates et al. a polymeric carbonylation catalyst system useful for the carbonylation of methanol including a polymer support containing pendant pyrrolidone groups which support a rhodium species. See also U.S. Pat. No. 5,281,359 to Scates et al. as well as U.S. Pat. No. 5,334,755 to Yoneda et al. and U.S. Pat. No. 5,364,963 to Minami et al.

So also, U.S. Pat. No. 5,155,261 to Marston et al. discloses an improved Monsanto type process for acetic acid preparation and a heterogeneous supported catalyst for accomplishing the same. The method comprises reacting methanol with carbon monoxide under a pressure of about 65 to 80 bar in a temperature of 170–200° C. in the presence of methyl iodide and the catalyst comprising an insoluble polymer having pendant free base, N-oxide, or quaternized pyridine groups supporting a rhodium species loaded to less than 10 weight percent (expressed as metal) of the polymer component.

WIPO Publication WO 98/57918 discloses a process for the production of acetic acid utilizing a vinyl pyridine supported Group VIII metal catalyst in a typical embodiment, about 9 percent by weight of vinyl pyridine is charged to the carbonylation reactor. See Example 1, p. 10.

Various supports have also been specifically suggested for supporting iridium catalyst. There is disclosed in U.S. Pat. No. 5,892,110 to Ramprasad et al. a process for producing acetic anhydride by the reaction of methyl acetate, carbon monoxide, and hydrogen at elevated temperatures and pressures in the presence of an alkyl halide and a heterogeneous bifunctional catalyst that contains an insoluble polymer having pendant quaternized phosphine groups some of which phosphine groups are ionically bonded to anionic Group VIII metal complexes, the remainder of the phosphine groups being bonded to iodide. The '110 patent reports that in contrast to earlier processes no accelerator (promoter) is necessary to achieve the catalytic reaction and the products are easily separated from the catalyst by filtration. The catalyst can be recycled for consecutive runs without loss in activity. In general the catalysts include a polymer, such as a polymer with pendant phosphine groups and a Group VIII metal such as rhodium or iridium. See column 2, lines 55–60. See also WIPO Publication 98-33590, and U.S. Pat. No. 4,127,506 to Gray et al.

The present invention utilizes polymer substrates with nitrogen containing repeat units to sequester, entrained or volatile catalyst species. In this way, entrained rhodium will not "plate out" in the carbonylation apparatus and volatile iridium complexes can be recovered.

SUMMARY OF INVENTION

There is provided in a first aspect of the present invention a carbonylation process for carbonylating a reactant including a reactor containing a reaction mixture which includes a Group VIII metallic catalyst component and an alkyl halide, which reactor is coupled to a flasher configured to continuously receive a stream of the reaction mixture and separate it into a product stream and a recycle reaction mixture stream wherein the process is improved by contacting the product stream with a polymeric resin having nitrogen containing heterocyclic repeat units operative to sequester the Group VIII metal catalyst components present in the product stream. Particularly preferred are pyridine ring-containing resins and pyrrolidone ring-containing resins. Typically vinyl pyridine and vinyl pyrrolidone resins are used and these resins are crosslinked a degree of crosslinking of at least about 20% so they are insoluble in the reaction medium. Most preferably the carbonylatable reactants are methanol or methyl acetate and the alkyl halide present in the reaction mixture is methyl iodide. The Group VIII catalyst component is typically selected from the group consisting of iridium, rhodium, cobalt, ruthenium or mixtures thereof. The invention is particularly useful in connection with iridium catalyzed systems.

The invention is likewise particularly useful for removing trace amounts of a Group VIII initial catalyst component from a product stream. Typically, such trace amounts may be from 1 part per billion (ppb) up to about 150 ppm, based on the Group VIII metal content. More typically, the invention is advantageously employed on a product stream having a Group VIII metal content of anywhere from about 5 ppb to about 5 ppm, based on the content of Group VIII metal.

In another aspect of the invention there is provided a carbonylation system ? a reactor coupled to a flasher which, in turn, is coupled to a product purification system wherein:

(a) the reactor contains a reaction mixture including a Group VIII metal catalyst component and an alkyl halide promoter component;

(b) the flasher is adapted to continuously receive a stream of the reaction mixture and separate it into a liquid recycle stream which is returned to the reactor and a vapor product stream which is supplied to the purification system and includes an entrained or volatile Group VIII metal catalyst component;

(c) there is further provided, downstream of the flasher, means for sequestering the Group VIII metal catalyst component from the product stream comprising a polymeric substrate having nitrogen containing heterocyclic repeat units.

Typically, the polymer substrate is in granular or bead form and is most preferably crosslinked, polyvinyl pyrrolidone resin which is insoluble in the reaction medium. Typically, the beads of resin are in a fixed bed between the flasher and the purification system such that the fixed bed of particulate resin contacts the product stream when it is in vapor form.

In a typical apparatus the flasher is configured to adiabatically vaporize the stream of reaction mixture provided to it so as to produce the vapor product stream as further discussed herein.

In still yet another aspect of the present invention there is provided a method of making acetic acid by way of the carbonylation of methanol including:

(a) reacting methanol with carbon monoxide in a reactor provided with a homogeneous reaction medium comprising a catalytic metal component selected from the group consisting of soluble forms of iridium, rhodium, and mixtures thereof, optionally including a co-promoter selected from the group consisting of ruthenium, osmium, tungsten, rhenium, zinc, cadmium, indium, mercury and mixtures thereof, and further including methyl acetate, methyl iodide and water;

(b) supplying a stream of the reaction mixture to a flasher adapted to separate the stream of the reaction mixture into a liquid recycle stream and a product stream;

(c) recycling the recycle stream to the reactor;

(d) contacting the product stream with a resin selected from the group consisting of vinylpyridine resins and vinyl-pyrrolidone resins and mixtures thereof, the resin being operative to sequester the catalytic metal components present in the product stream and;

(e) purifying the product stream.

BRIEF DESCRIPTION OF DRAWING

The invention is described in detail below with reference to the single FIGURE which is a schematic diagram illustrating a carbonylation apparatus which may be used in connection with the present invention.

DESCRIPTION OF THE PREFERRED EMBODIMENTS

The present invention is directed generally to carbonylation systems which employ Group VIII metal catalyst components. Without desiring to be bound by any theory, it is believed that the catalyst component in the form of an anionic metal carbonyl complex electrostatically binds to the cationic sites of the polymer substrate which is generated by the reaction of the alkyl iodides on the substrate, to quaternize nitrogen containing heterocyclic repeat units on a polymer substrate. Thus, in accordance with the invention entrained or volatile catalyst species are immobilized on the resin and may be recovered by digesting the polymer i.e. by combustion or any other suitable means. The present invention may be appreciated in connection with, for example, the carbonylation of methanol, its reactive derivatives with carbon monoxide in a homogeneous catalytic reaction system comprising a reaction solvent (typically acetic acid), methanol and/or its reactive derivatives, a soluble iridium catalyst, at least a finite concentration of water, as well as an insoluble pyridine or pyrrolidone ring containing polymer and optionally including an osmium or ruthenium promoter. The carbonylation of methanol utilizing iridium catalyst is well known and is generally described in the following U.S. Pat. Nos.: 5,942,460; 5,932,764; 5,883,295; 5,877,348; 5,877,347 and 5,696,284, the disclosures of which are hereby incorporated by reference into this application as if set forth in their entirety.

Suitable reactive derivatives of methanol include methyl acetate, dimethyl ether and methyl iodide. A mixture of methanol and reactive derivatives thereof may be used as reactants in the process of the present invention. Preferably, methanol and/or methyl acetate arc used as reactants. At least some of the methanol and/or reactive derivative thereof will be converted to, and hence present as, methyl acetate in the liquid reaction composition by reaction with acetic acid product or solvent. The concentration in the liquid reaction composition of a methyl acetate is suitably in the range of about 1 to 70% by weight, preferably about 2 to 50% by weight, most preferably about 3 to 35% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water in the liquid reaction composition is in the range of about 0.1 to 15% by weight, more preferably about 1 to 15% by weight, most preferably about 1 to 10% by weight.

An iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. More preferably, chloride-free complexes of iridium such as acetates, oxalates and acetoacetates are employed.

Preferably, the iridium catalyst concentration in the liquid reaction composition is in the range of about 100 to 6000 ppm by weight of iridium.

Promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium and mercury, and are more preferably selected from ruthenium and osmium. Ruthenium is the most preferred promoter. Preferably, the promoter is present in an effective amount up to the limit of its solubility in the liquid reaction composition and/or any liquid process streams recycled to the carbonylation reactor from the acetic acid recovery stage. The promoter is suitably present in the liquid reaction composition at a molar ratio of promoter to iridium of about [0.5 to 15]:1, preferably about [2 to 10]:1, more preferably about [2 to 7.5]:1. A suitable promoter concentration is 400 to 5000 ppm.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form. Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]n$, $[Ru(CO)_4I_2]$, $[Ru(CO)_3I_2]_2$, tetra(aceto)chlorouthenium(II,III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium (II), tetrachlorobis(benzene) diruthenium(II), dichloro(cycloocta-1,5 diene)ruthenium (II) polymer and tris(acetylacetonate)ruthenium (III).

Examples of suitable osmium-containing compounds which may be used as sources or promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$, pentachloro-$\mu$-nitrodiosmium and mixed osmium halocarbonyls such as tricarbonyldichloroosmium (II) dimer and other organoosmium complexes.

Examples of suitable tungsten-containing compounds which may be used as sources of promoter include $W(CO)_6$, $WCl_4$, $WCl_6$, $WBr_6$, $WI_2$, or $C_9H_{12}W(CO)_3$ and any tungsten chloro-, bromo- or iodo-carbonyl compound.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3xH_2O$, $[Re(CO)_4I]_2$, $Re(CO)_4I_2]^-H^+$ and $ReCl_5$—$yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$ and $Hg_2Cl_2$.

Examples of zinc-containing compounds which may be used as sources of promoter include $Zn(OAc)_2$, $Zn(OH)_2$, $ZnI_2$, $ZnBr_2$, $ZnCl_2$ and zinc acetylacetonate.

Examples of suitable gallium-containing compounds which may be used as sources of promoter include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium acetate, $InCl_3$, $InBr_3$, $InI_3$, $InI$ and $In(OH)_3$.

Preferably, the concentration of methyl iodide in the liquid reaction composition is in the range of about 1 to 50% by weight, preferably about 2 to 30% by weight.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range of about 1 to 70 bar, preferably about 1 to 35 bar, and most preferably about 1 to 15 bar.

The pressure of the carbonylation reaction is suitably in the range of 10 to 200 Bar, preferably about 10 to 100 Bar, most preferably about 15 to 50 Bar. The temperature of the carbonylation reaction is suitably in the range of about 100 to 300° C., preferably in the range about 150 to 220° C.

Acetic acid is typically used as the solvent for the reaction.

The terminology "pyridine ring-containing polymer", "pyridine polymer" and the like used herein is intended to refer to a polymer containing substituted or non-substituted pyridine rings or substituted or non-substituted, pyridine-containing polycondensed rings such as quinoline rings. The substituents include those inert to the methanol carbonylation such as an alkyl group and alkoxy group. Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and divinylbenzene, copolymers of styrene, vinylbenzene and divinylbenzene, copolymers of vinylmethylpyridine and divinylbenzene and copolymers of vinylpyridine, methyl acrylate and ethyl diacrylate. Particularly preferred polymers are described in U.S. Pat. No. 5,334,755 to Yoneda et al., the disclosure of which is incorporated herein by reference. Relatively high degrees of crosslinking in the polymer is most preferred.

The terminology "pyrrolidone ring-containing polymer", pyrrolidone polymer and the like used herein is intended to refer to a polymer containing substituted or non-substituted pyrrolidone rings. The substituents may include those inert to the methanol carbonylation medium such as alkyl groups or alkoxy groups. Typical examples of insoluble, pyrrolidone ring-containing polymer include those obtained by reaction of vinyl pyrrolidone with a di-vinyl monomer-containing vinyl monomer such as a co-polymer of a vinyl pyrrolidone and divinyl benzene. Pyrrolidone polymers are discussed in U.S. Pat. No. 5,466,874 of Scates et al as well as U.S. Pat. Nos. 5,286,826; 4,786,699 and 4,139,688, the disclosures of which are incorporated herein by reference. A preferred pyrrolidone polymer substrate is available under the trade name of Reillex® from Reilley Tar and Chemical Corporation of Indianapolis, Ind.

It is desirable that the above nitrogen heterocyclic ring-containing polymer should be crosslinked by at least 10%, preferably at least about 15% or 20% and up to about 75%. A degree of crosslinking below 10% is disadvantageous because the mechanical strength of the polymer may degrade during use. As the degree of crosslinking increases, the availability of the polymer surface may be unduly restricted. A maximum degree of crosslinking of 50 or 60 percent is then preferred. The term "degree of crosslinking" used herein is intended to refer to the content, in terms of % by weight, of the divinyl monomer, for example.

A pyridine or pyrrolidone insoluble polymer may be in the free base or N-oxide form or quaternized form as noted above. The insoluble, pyridine or pyrrolidone ring-containing polymer is preferably in a bead or granular form, more preferably in a spherical form, having a particle diameter of about 0.01–2 mm, preferably about 0.1–1 mm, more preferably about 0.25–0.7 mm. Commercially available pyridine-containing polymers such as Reillex-425 (product of Reilly Tar and Chemical Corporation) and KEX-316, KeX-501 and KEX-212 (products of Koei Chemical Co., Ltd.) may be suitably used for the purpose of the present invention. As noted above pyrrolidones are also available from Reilly Tar and a degree of crosslinking of at least about 10% is preferred.

The present invention is better appreciated by reference to FIG. 1 which is a schematic diagram illustrating a typical carbonylation system. FIG. 1 there is shown a carbonylation system 10 including a reactor 12 provided with a vent 14. Reactor 12 is coupled to a flasher 16 by way of a conduit 18. The flasher, in turn, is coupled to a purification section 198 which comprises generally a light ends column 20, a dehydration column 22 and a heavy ends column 24. In accordance with the invention there is provided a fixed bed of pyrrolidone or pyridine resin in granular form indicated at 30. Fixed bed 30 is operative to sequester entrained or volatile catalyst species such as volatile iridium which exits the flasher via the vapor or product stream.

Acetic acid is manufactured in a liquid phase reaction at a temperature of from about 150–200° C. and a pressure of from about 30 to about 60 bar. Carbon monoxide and methanol are introduced continuously into reactor 12 with adequate mixing at a high carbon monoxide partial pressure. The non-condensable bi-products are vented from the reactor to maintain an optimum carbon monoxide partial pressure. The reactor off gas is treated to recover reactor condensables i.e. methyl iodide before flaring. Methanol and carbon monoxide efficiencies are preferably greater than about 98 and 90% respectively. As will be appreciated from the Smith et al. patent noted above, major inefficiencies of the process are the concurrent manufacture of carbon dioxide and hydrogen by way of the water gas shift reaction.

From the reactor a stream of the reaction mixture is continuously fed via conduit 18 to flasher 16. Through the flasher the product acetic acid and the majority of the light ends (methyl iodide, methyl acetate, water) are separated from the reactor catalyst solution and forwarded with dissolved gases to the distillation or purification section in adiabatic single stage reaction. The catalyst solution is recycled to the reactor via conduit 32. Under the process conditions of the flash, the catalyst is susceptible to deactivation at the low carbon monoxide partial pressures in the flash vessel, and may be entrained to purification system 19.

The purification of the acetic acid typically requires distillation in a three column process. The vapor product from the flasher overhead is first passed through a fixed bed 30 of pyrrolidone, pyridine or other nitrogen containing resin so as to remove the entrained or the volatile Group VIII metal catalyst species present before being fed to a light ends column. Methyl iodide, methyl acetate, and a portion of the water condense overhead in the light end columns to form two phases (organic and aqueous). Both overhead phases return to the reaction section via recycle line 34. The dissolved gases from the light ends column vent through the distillation section. Before this vent stream is flared, residual light ends are scrubbed and recycled to the process. The aqueous acetic acid side draw off from the light end column feeds dehydration column 22. Water and some acetic acid from this column separate and recycle to the reaction system via recycle line 34 as shown. The dry crude acetic acid is a residue stream from this column which feeds heavy ends column 24. The product acetic acid is afforded as a vapor side draw off of the heavy ends column as shown. A mixture of high boiling acetic by-products primarily propionic acid are removed as bottoms from the column.

There is optionally provided another fixed bed 36 which is employed to control the iodide, especially alkyl iodide, content of the product. One type of fixed bed may be a vinylpyridine fixed bed as is disclosed in European Patent Publication 0 685 445 of Fillers et al.; whereas, a particularly preferred method of removing iodide involves the use of a macro-reticular silver-exchanged, strong acid ion exchange resin as described in U.S. Pat. No. 4,615,806 to Hilton.

It has been demonstrated that vinyl pyrrolidone resins will bind rhodium catalyst components, for example, in U.S. Pat. No. 5,466,874 to Scates et al.; whereas, vinylpyridine resins will likewise bind rhodium catalyst components as described in U.S. Pat. No. 5,155,261 to Marston et al. The '874 and '261 patents are incorporated herein by reference. In order to ascertain whether iridium and ruthenium catalysts would bind to these resins and whether or not these resins might be useful as a means for sequestering volatile or entrained Group VIII metal catalyst components, the following experiments were performed.

General Procedure

A series of runs were carried out in a 300 cc Hostalloy B batch autoclave (Autoclave Engineering). Each run lasted about 30 minutes and was conducted at a reactor temperature of about 195° C. and a carbon monoxide pressure of about 400 psig. The procedure for all runs in Table I is described below.

The reactants were weighed and charged to the reactor. In the reactor, the solution consisted of water (3.8 g), glacial acetic acid (60.4 g), Iridium (IV) oxide hydrate (3000 ppm, 0.6 g,) (PPG Industries), methyl acetate (33.7 g) (Aldrich) (which equilibrates with methanol and acetic acid), and methyl iodide (20.4 g) (Fisher). The reactor was purged several times with 50 psig of carbon monoxide. After ensuring the reactor was leak free, the reactor was pressurized to 270 psig and heated to 195° C. Temperature of the reactor was maintained at 195° C., varying by less than 1° C. The temperature was maintained by using an electric heater and adjusted further by cooling water. As the temperature increased, the reactor pressure was raised to 400 psig by adding carbon monoxide from the reservoir. When the reactor solution reached the target conditions, the stirrer was turned on at 800 rpm. Carbon monoxide from the reservoir was introduced to the reactor on pressure demand to maintain 400 psig. This time was recorded as time zero. The carbon monoxide uptake from the reservoir, reactor temperature and reactor pressure were recorded every minute. When carbon monoxide uptake had stopped, the run was completed and the reaction solution was allowed to cool to room temperature.

The rate of gas uptake was measured by plotting the carbon monoxide consumed as a function of time. This rate of gas uptake was then used to calculate the carbonylation rate, as number of moles of reactant consumed per liter of cold degassed reactor liquid per hour (mol/l/hr) as space time yield (STY), at a particular reactor composition.

EXAMPLES

Comparative Example A

The above procedure was followed without the addition of a nitrogen-heterocycle containing polymer. Results appear in Table I.

Example 1

The above procedure was followed wherein 1.3 g of 25% crosslinked poly(4-vinylpyridine) ("PVP-I") (Aldrich, Reilly), about 1%, was added. The carbonylation rate was measured approximately as 43 STY on the same basis as Comparative Example A. After completion of the run, the polymer was digested and analyzed for iridium metal in order to determine the amount of Iridium charged which had been anchored to the polymer. Results for this Example also appear in Table I, along with the results of Examples 2–8.

Examples 2–8

Following the procedure of Example 1, a series of runs were carried out with different amounts of poly(vinyl pyridine). Polyvinylpyridine was supplied by either Aldrich or Reilly Industries (Indianapolis. Ind.). Reactor compositions and results as to anchored iridium appear in Table I.

As can be seen, best results in terms of sequestering the catalyst are obtained when the ratio of resin to Group VIII metal catalyst is relatively high as is the case in a fixed bed disposed in a product stream in accordance with the invention.

TABLE I

Effect of Polymer, Polyvinylpyridine on 3000 ppm Iridium

|   | [1]PVP-I (wt %) | STY (mole/L-Hr) | [2]Ir in PVP-I (% Ir) |
|---|---|---|---|
| A | 0.0% | 31 | 0% |
| 1 | 1.00% | 43 | 10% |
| 2 | 0.05% | 37 | 3% |
| 3 | 0.10% | 43 | 4% |
| 4 | 0.40% | 47 | 7% |
| 5 | 0.50% | 43 | 8% |
| 6 | 0.70% | 36 | 8% |
| 7 | 2.5% | 20 | 33% |
| 8 | 4.00% | 11 | 97% |

[1]Amount of polyvinylpyridine (PVP-I) in wt % in the reactor. Experiments were done at 195° C.; 400 psia. The reactor materials included approximately 3.0% $H_2O$; 27% MeOAc; 20% MeI and 3000 ppm Ir.
[2]Ir in the polymer is listed in % of Ir. Samples were digested in acid and analyzed for metal. % Ir = {(initial amount of Ir) − (Ir anchored in the polymer)}/(Initial amount of Ir).

Examples 9–14

Following generally the procedure set forth above, crosslinked polyvinyl pyrrolidone resin was charged to an autoclave along with the various components listed in Table II below.

TABLE II

STY of carbonylation with Ir- or Ir/Ru-catalyst and polyvinyl pyrrolidone.

| Example | PVP-o | Ir | Ru | Ir anchored* | Ru anchored* | STY (mole/L-hr) |
|---|---|---|---|---|---|---|
| 9 | 4 | 1000 | 0 | 1000 | 0 | 0 |
| 10 | 4 | 2000 | 0 | 1970 | 0 | 0 |
| 11 | 4 | 6000 | 0 | 5900 | 0 | 0 |
| 12 | 0.4 | 6000 | 7000 | 2750 | 1000 | 53 |
| 13 | 4 | 6000 | 6000 | 5900 | 5500 | 14 |
| 14 | 4 | 2000 | 2000 | 2050 | 2000 | 3 |

*After the reaction, the polymer was filtered, digested and analyzed for the amount of Ir and/or Ru in the polymer. Anchored ppm refers to ppm initially present in the reactor.

The invention has been described in detail and illustrated in connection with numerous embodiments. Modifications to specific embodiments within the spirit and scope of the present invention will be readily apparent to those of skill in the art. For example, a rhodium co-catalyst could be used with the iridium or rhodium could be used as the only catalyst metal. Such modifications are within the spirit and scope of the present invention which is set forth in the appended claims.

What is claimed is:
1. A carbonylation process comprising:
 (a) carbonylating a reactant in the presence of a Group VIII metal catalyst component and an alkyl halide promoter component to form a reaction mixture in a reactor;
 (b) supplying a stream of the reaction mixture to a flasher, coupled to the reactor, to separate the stream of the reaction mixture into a liquid recycle stream and a product stream;
 (c) contacting the product stream with a polymeric resin comprising nitrogen containing heterocyclic repeat units operative to sequester, on the polymeric resin, at least a portion of the Group VIII metal catalyst component present in the product stream; and

(d) recovering the at least a portion of the Group VIII metal component by separating the at least a portion of the Group VIII metal component from the polymeric resin.

2. The process of claim 1, wherein the polymeric resin is selected from the group consisting of pyridine ring-containing resins and pyrrolidone ring-containing resins.

3. The process of claim 2, wherein the polymeric resin is a vinyl pyridine resin.

4. The process of claim 3, wherein the polymeric resin is a crosslinked vinyl pyridine resin having a degree of crosslinking of at least about 10%.

5. The process of claim 2, wherein the polymeric resin is a polyvinyl pyrrolidone resin.

6. The process of claim 5, wherein the polymeric resin is a vinyl pyrrolidone resin having a degree of crosslinking of at least about 10%.

7. The process of claim 1, wherein the alkyl halide is methyl iodide.

8. The process of claim 1, wherein the Group VIII metal catalyst component is selected form the group consisting of iridium, rhodium, cobalt, ruthenium, and mixtures thereof.

9. The process of claim 8, wherein the Group VIII metal catalyst component comprises rhodium.

10. A carbonylation process comprising:

(a) carbonylating a reactant in the presence of a Group VIII metal catalyst component comprising iridium and an alkyl halide promoter component to form a reaction mixture in a reactor;

(b) continuously supplying a stream of the reaction mixture to a flasher, coupled to the reactor, to separate the stream of the reaction mixture into a liquid recycle stream and a product stream; and (c) contacting the product stream with a polymeric resin comprising nitrogen containing heterocyclic repeat units operative to sequester, on the polymeric resin, at least a portion the Group VIII metal catalyst component present in the product stream.

11. A method for producing acetic acid by way of the carbonylation of methanol comprising:

(a) reacting methanol with carbon monoxide in a reactor provided with a homogeneous reaction medium comprising a catalytic metal component selected from the group consisting of soluble forms of iridium, rhodium and mixtures thereof, optionally including a co-promoter selected from the group consisting of ruthenium, osmium, tungsten, rhenium, zinc, cadmium, indium, mercury and mixtures thereof and further comprising methyl acetate, methyl iodide and water;

(b) supplying a stream of the reaction mixture to a flasher, coupled to the reactor, to separate the stream of the reaction mixture into a liquid recycle stream and a product stream;

(c) recycling the recycle stream to the reactor;

(d) contacting the product stream with a resin selected from the group consisting of crosslinked vinyl pyridine resins and crosslinked vinyl pyrrolidone resins and mixtures thereof to sequester, on the resin, at least a portion of the catalytic metal component present in the product stream;

(e) purifying the product stream; and (f) recovering the at least a portion of the catalytic metal component by separating the at least apportion of the catalytic metal components from the resin.

12. The method of claim 11, wherein the resin is a crosslinked vinyl pyrrolidone resin.

13. A method for producing acetic acid by way of the carbonylation of methanol comprising:

(a) reacting methanol with carbon monoxide in a reactor provided with a homogeneous reaction medium comprising a catalytic metal component selected from the group consisting of soluble forms of iridium, rhodium and mixtures thereof, optionally including a co-promoter selected from the group consisting of ruthenium, osmium, tungsten, rhenium, zinc, cadmium, indium, mercury and mixtures thereof and further including methyl acetate, methyl iodide and water;

(b) continuously supplying a stream of the reaction mixture to a flasher, coupled to the reactor, to separate the stream of the reaction mixture into a liquid recycle stream and a vapor product stream;

(c) recycling the recycle stream to the reactor;

(d) contacting the vapor product stream with a resin selected from the group consisting of crosslinked vinyl pyridine resins and crosslinked vinyl pyrrolidone resins and mixtures thereof to sequester at least a portion of the catalytic metal component present in the product stream on the resin; and (e) purifying the product stream.

14. The method of claim 13, wherein the catalytic metal component comprises iridium.

15. The method of claim 12, wherein the catalytic metal component comprises ruthenium.

* * * * *